(12) United States Patent
Nilsson (10) Patent No.: US 10,977,665 B2
(45) Date of Patent: Apr. 13, 2021

(54) PROVENANCE TRACKING USING GENETIC MATERIAL

(71) Applicant: Intertrust Technologies Corporation, Sunnyvale, CA (US)

(72) Inventor: Jarl Nilsson, Mountain View, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 0 days.

(21) Appl. No.: 16/788,070

(22) Filed: Feb. 11, 2020

(65) Prior Publication Data

US 2020/0175527 A1 Jun. 4, 2020

Related U.S. Application Data

(63) Continuation of application No. 15/664,967, filed on Jul. 31, 2017, now Pat. No. 10,586,239.

(Continued)

(51) Int. Cl.
| | |
|---|---|
| *G06Q 30/00* | (2012.01) |
| *G06K 7/10* | (2006.01) |
| *C12Q 1/6879* | (2018.01) |
| *G16B 30/00* | (2019.01) |
| *G06Q 50/18* | (2012.01) |
| *G06K 19/06* | (2006.01) |
| *G16B 50/40* | (2019.01) |

(52) U.S. Cl.
CPC ....... *G06Q 30/0185* (2013.01); *C12Q 1/6879* (2013.01); *G06K 7/10* (2013.01); *G16B 30/00* (2019.02); *G06K 2019/06234* (2013.01); *G06Q 50/184* (2013.01); *G16B 50/40* (2019.02)

(58) Field of Classification Search
CPC ............. G06Q 30/018; G06Q 30/0185; G06Q 50/184; G06F 19/22; G06K 2019/06234; C12Q 2563/179; C12Q 2563/185; D21H 21/40; D21H 21/44; D21H 21/46; G06N 3/12; G06N 3/123
See application file for complete search history.

(56) References Cited

U.S. PATENT DOCUMENTS

| 9,852,393 B2 * | 12/2017 | Walden ................ C07D 311/80 |
| 2002/0055118 A1 * | 5/2002 | Eym .................... A44B 15/005 |
| | | 435/6.12 |

(Continued)

FOREIGN PATENT DOCUMENTS

WO    WO-2015050899 A1 *    4/2015    ............... C12Q 1/68

*Primary Examiner* — Thien M Le
*Assistant Examiner* — April A Taylor
(74) *Attorney, Agent, or Firm* — Finnegan, Henderson, Farabow, Garrett & Dunner LLP (57) ABSTRACT

Systems and methods for provenance tracking and/or identification of a product using genetic material are claimed. In various embodiments, genetic material such as plasmids may be incorporated into and/or otherwise persistently associated with a product. The genetic material may be encoded with, among other things, information that may uniquely identify the product, provide details relating to the origins of the product, the handling, distribution, and/or chain of custody of the product, intellectual property rights and/or other rights associated with the product, and/or the like. By extracting and analyzing the genetic material from the product, information encoded in the genetic material may be obtained by an interested party.

20 Claims, 4 Drawing Sheets

Related U.S. Application Data

(60) Provisional application No. 62/371,505, filed on Aug. 5, 2016.

(56) References Cited

U.S. PATENT DOCUMENTS

| | | | | |
|---|---|---|---|---|
| 2004/0043390 | A1* | 3/2004 | Stadler | B82Y 10/00 435/6.11 |
| 2014/0356858 | A1* | 12/2014 | Harman | C12Q 1/68 435/5 |
| 2015/0083797 | A1* | 3/2015 | Tran | G09F 3/0298 235/375 |
| 2015/0141264 | A1* | 5/2015 | Jung | C12Q 1/68 506/2 |
| 2018/0108024 | A1* | 4/2018 | Greco | H04L 9/0637 |
| 2019/0241888 | A1* | 8/2019 | Macula | C12Q 1/6806 |

* cited by examiner

PROVENANCE TRACKING USING GENETIC MATERIAL

RELATED APPLICATIONS

This application is a continuation of U.S. application Ser. No. 15/664,967, filed Jul. 31, 2017, titled PROVENANCE TRACKING USING GENETIC MATERIAL, which issued as U.S. Pat. No. 10,586,239, and claims the benefit of priority under 35 U.S.C. § 119(e) to U.S. Provisional Patent Application No. 62/371,505, filed Aug. 5, 2016, and titled "SYSTEMS AND METHODS FOR PROVENANCE TRACKING USING GENETIC MATERIAL," both of which are hereby incorporated by reference in their entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY

The present disclosure relates generally to systems and methods for associating and identifying information relating to the product. More specifically, but not exclusively, the present disclosure relates to systems and methods for associating and identifying information relating to a product using genetic material.

Information regarding product may be used in a variety of applications. For example, provenance information detailing the origins and/or chain of custody of a product may be useful in determining whether a product is a genuine or a counterfeit product. Similarly, information relating to a product's chain of custody may be beneficial in determining whether a product is handled in accordance with certain regulatory and/or licensing requirements. Tracking the origins and/or chain of custody of a product using conventional product identification tags, however, may be relatively cumbersome.

System and methods disclosed herein allow for, among other things, association of information with a product using genetic material. Such product information may comprise, among other things, information relating to a provenance of the product (e.g., origin and/or chain of custody). Once associated with a product, the genetic material may be later extracted and/or analyzed to determine the associated information (e.g., provenance information and/or the like).

In various embodiments, genetic material such as, for example, plasmids, may be incorporated into and/or otherwise persistently associated with various products. The genetic material may be encoded with, among other things, information that may uniquely identify the product, provide details relating to the origins of the product, the handling, distribution, and/or chain of custody of the product, intellectual property rights and/or other rights associated with the product, and/or any provide other information relating to the product. By extracting and analyzing the genetic material from the product, information encoded in the genetic material may be obtained by an interested party.

BRIEF DESCRIPTION OF THE DRAWINGS

The inventive body of work will be readily understood by referring to the following detailed description in conjunction with the accompanying drawings, in which.

DETAILED DESCRIPTION

A detailed description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals or descriptions. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure but is merely representative of possible embodiments of the disclosure. In addition, the steps of any method disclosed herein do not necessarily need to be executed in any specific order, or even sequentially, nor need the steps be executed only once, unless otherwise specified.

Genetic material may be used to encode information. For example, artificial plasmids—small, circular, double-stranded DNA molecules distinct from chromosomal DNA that can replicate independently—may be used to encode various types of information. Plasmids may occur naturally in certain bacteria and eukaryotic cells. Plasmids may vary in length from thousands of DNA base pairs to hundreds of thousands of base pairs.

Artificial plasmids may be manufactured to specification using a variety of suitable methods. Among other uses, artificial plasmids may be used as vectors in molecular cloning that drive the replication of recombinant DNA sequences. Consistent with various disclosed embodiments, product information may be encoded in genetic sequences included in a generated plasmid. Such product information may comprise, for example, one or more of information relating to a product (e.g., information identifying a product type, model, serial number, origin, etc.), information relating to a handling and/or distribution of the product (e.g., provenance information), information relating to real and/or intellectual property rights associated with the product, and/or any other desirable information relating to the product. In some embodiments, a variety of suitable methods may be used to insert encoded genetic information into plasmids that may depend, at least in part, on a type of a target plasmid.

In certain disclosed embodiments, generated plasmids encoding product information may be inserted in, deposited on, and/or otherwise physically associated with a product, and may function as a genetic tag and/or marker for the product. Although various embodiments disclosed herein are discussed in connection with using plasmids to encode product information in an associated genetic sequence, it will be appreciated that a variety of other suitable types of genetic material may also be used in connection with the disclosed systems and methods, such as, for example, innocuous bacteria.

Generated plasmids encoding product information may be introduced to a product during its manufacture and/or at various points during its chain of distribution and/or use. At various times during the distribution and/or chain of use of the product, the genetic information encoded by the plasmids may be extracted and/or isolated from the product. The extracted product information may be used in a variety of applications and/or contexts, including any of the applications and/or contexts described herein. In certain embodiments, the extracted product information may provide information which may be used to access more detailed information relating to a product, its provenance, its chain of custody, and/or the like. For example, the extracted product information may provide a link to a website and/or other networked computer location providing more detailed information relating to a product.

Product Tagging and Information Extraction Overview

Figure 1:
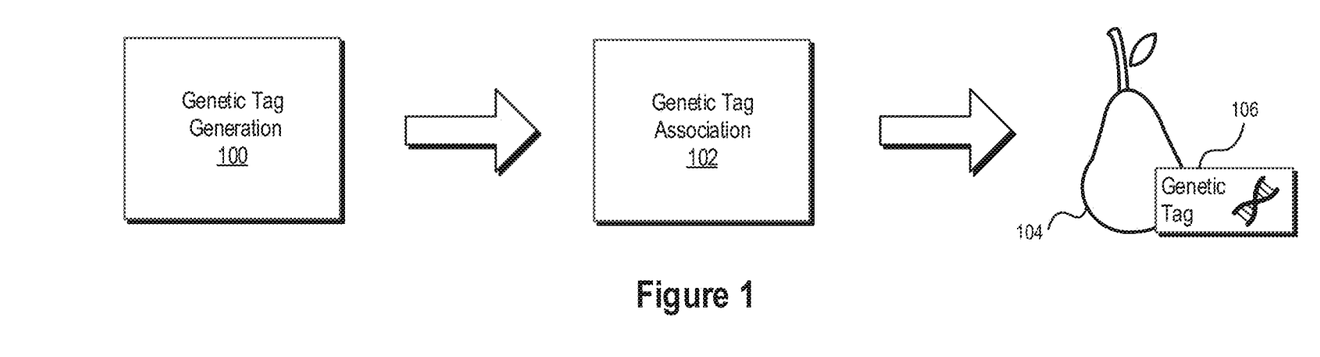
FIG. 1 illustrates a simplified conceptual diagram of a tagging product with a genetic tag consistent with embodiments of the present disclosure.

FIG. 1 illustrates a simplified conceptual diagram of tagging a product 104 with a genetic tag 106 consistent with embodiments of the present disclosure. Although embodiments disclosed herein are discussed in connection with a provenance tracking and/or identification process for a product 104, further embodiments may be used in connection with product chain of custody tracking and/or identification, product information distribution, product registration, product ownership management and/or enforcement, property rights management and/or enforcement, and/or any other suitable process, application, and/or context.

As illustrated, genetic material may be generated 100 that encodes information relating to a product 104 in a synthesized genetic sequence. This information may comprise any of the types of product information disclosed herein. In certain embodiments, the genetic material may comprise one or more artificial plasmids. The generated material may function as a genetic tag 106. Although certain embodiments disclosed herein are described as using plasmids in connection with encoding and distributing genetic information, it will be appreciated that any other suitable type of genetic material that encodes product information in a synthesized genetic sequence may also be used.

The product 104 may comprise any product and/or item including, without limitation, biological products (e.g., cell lines, germlines, etc.), agricultural products (e.g., fruits, vegetable, seeds, poultry, livestock, etc.), manufactured food products, clothing and/or accessories (e.g., handbags, etc.), parts, pharmaceuticals, electronic devices, and/or any other type of product and/or item that may be persistently and/or substantially persistently associated with a genetic tag 106 consistent with embodiments disclosed herein.

Generated genetic tags 106 may be inserted in and/or otherwise included on a product during its manufacture and/or at some point during its chain of distribution and/or use. In some embodiments, in connection with a non-agricultural product 104 (e.g., a handbag or the like), a genetic tag 106 such as a plasmid may be incorporated in a material and/or a component of the product 104 during manufacture of the material and/or component. In certain embodiments, genetic tags 106 may be inserted in and/or disposed on a surface of a product 104 and/or a component thereof. For example, in some embodiments, plasmids functioning as genetic tags 106 may be disposed on a surface of a product 104 via an aerosol and/or the like.

In some embodiments, generated genetic tags 106 may be introduced into cells included in biological and/or agricultural products (e.g., a fruit product 104). When plasmids are introduced into live cells, the plasmid may persist and/or be reproduced by the cells during division. For example, if a plasmid is introduced into a live germ line, the plasmid may persist in the line. Similarly, if the plasmid is inserted into live somatic cells, the plasmid marker will be replicated for the at least the lifespan of the organism. When a live cell divides, plasmids included in the cell may be copied such that each daughter cell may receive a copy of each plasmid. If the plasmid is inserted into dead cells, the plasmid may persist in the dead cells but not be replicated.

Generated genetic tags 106, including plasmids, may be inserted in and/or otherwise included on a product 104 using a variety of methods. For example, as noted above, genetic tags 106 may be deposited on a surface of a product 104 via an air stream, a needle, a swab, an aerosol, and/or any other carrier medium (e.g., within a bacterium). In some embodiments, genetic tags 106 may be incorporated into a material used in the product 104 during manufacture of the product 104 and/or its constituent materials and/or components (e.g., mixed into a liquid plastic material and/or the like). In further embodiments, a gene gun and/or a biolistic particle delivery system may be used to inject genetic tags 106 such as plasmids into cells.

Figure 2:
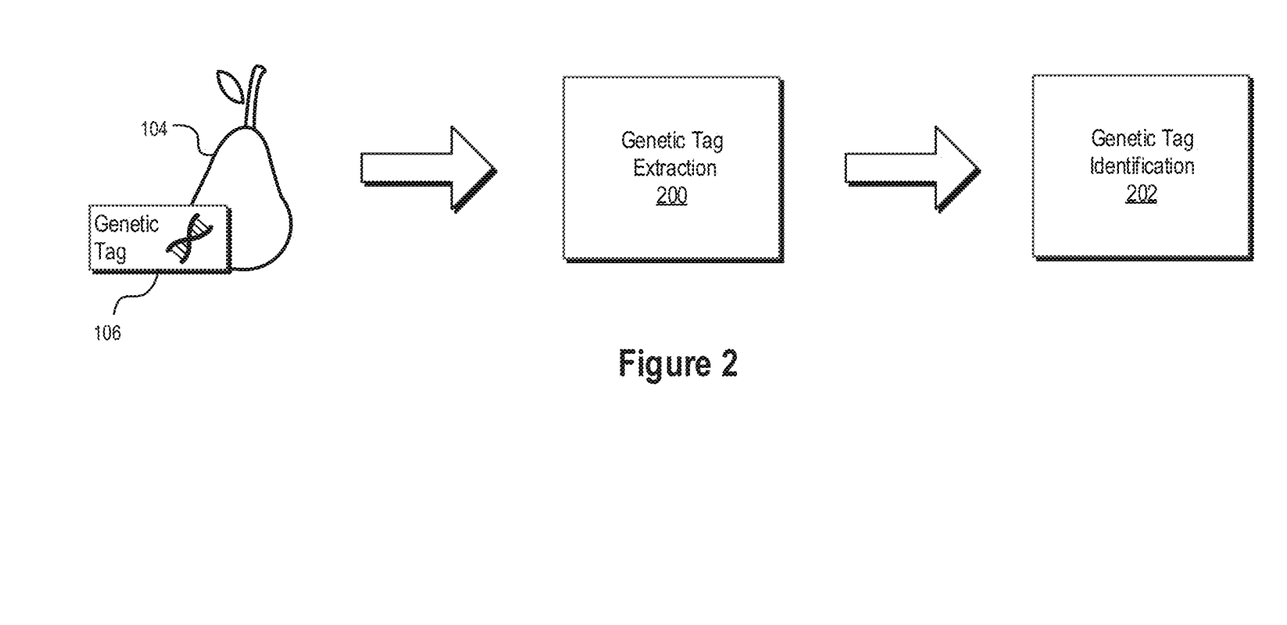
FIG. 2 illustrates a simplified conceptual diagram of extracting information from a tagged product consistent with embodiments of the present disclosure.

Once a product 104 has been persistently and/or substantially persistently marked with a genetic tag 106, the genetic information included in the genetic tag 106 may be extracted from the product. FIG. 2 illustrates a simplified conceptual diagram of extracting information from a tagged product 104 consistent with embodiments of the present disclosure. A variety of suitable processes may be used to extract 200 the genetic tag 106 from the product 104. In certain embodiments, any genetic material extracted from the genetic tag 106 may be amplified and/or reproduced to assist in analysis of the extracted genetic material. For example, in some embodiments, polymerase chain reaction ("PCR") processes may be used to amplify genetic information included in a plasmid by several orders of magnitude, generating additional copies of the genetic information included in the plasmid to aid in analysis.

Extracted genetic information from the genetic tag 106 may be analyzed to identify certain product information encoded therein 202. In certain embodiments, the product information may be obtained directly from the extracted genetic information encoded in the genetic tag 106. In further embodiments, information relating to a location of product information may be obtained from the extracted genetic information encoded in the genetic tag 106 (e.g., a location in a product database, a website, and/or the like). In such embodiments, identifying the product information may comprise accessing the information from a location identified by information encoded in the genetic tag 106.

Genetic Material Generation and Product Tagging

Figure 3:
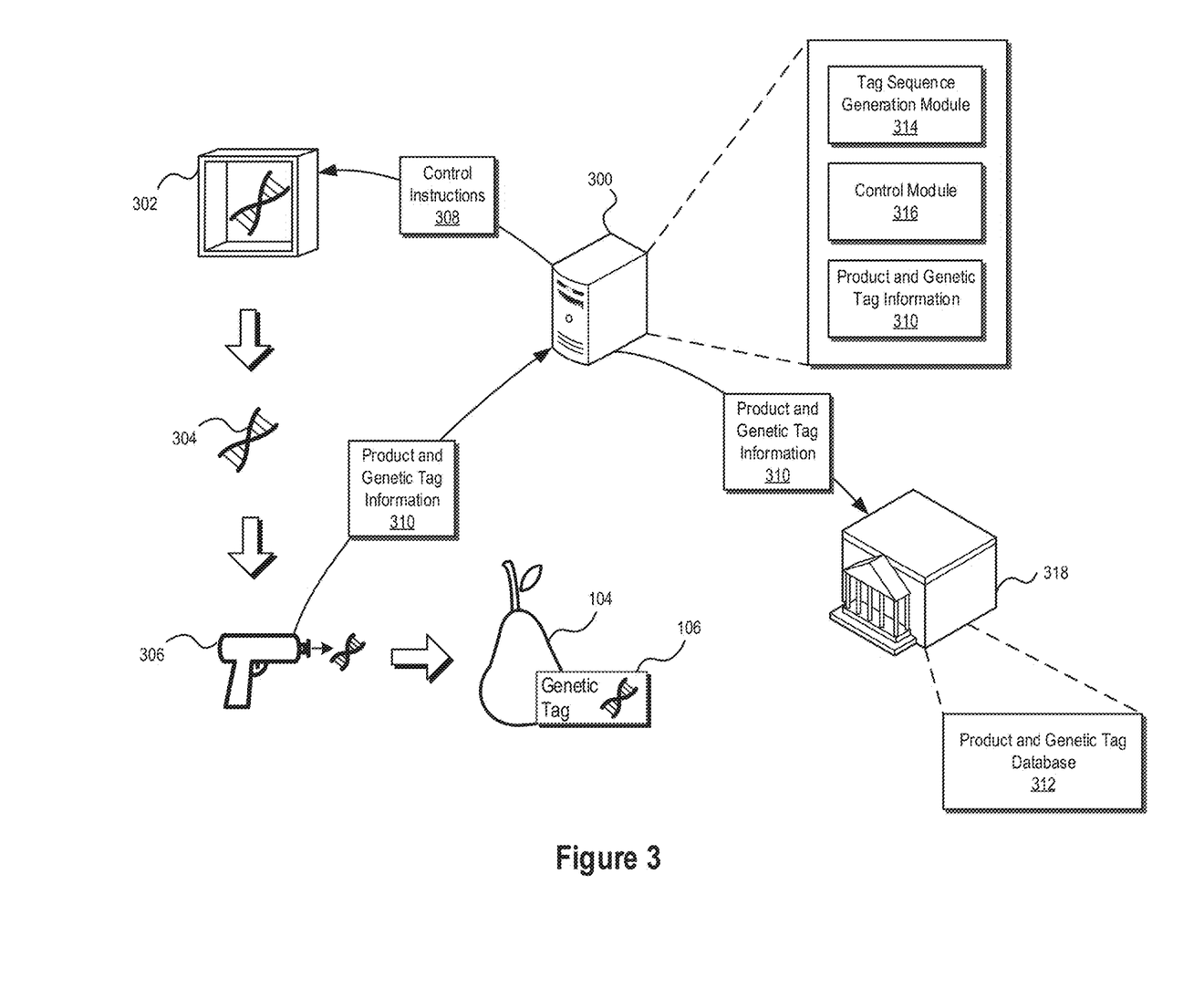
FIG. 3 illustrates tagging of a product with genetic material consistent with embodiments of the present disclosure.

FIG. 3 illustrates tagging of a product 104 with genetic material 304 consistent with embodiments of the present disclosure. Consistent with embodiments disclosed herein, genetic material 304 may be synthesized by a genetic material synthesis system 302 and encoded with information relating to a product 104. For example, an artificial plasmid may be generated by the genetic material synthesis system 302 encoded with product information in a synthesized genetic sequence. As discussed in more detail below, the genetic material 304 may be persistently and/or substantially persistently associated with the product 104 and may function as a genetic tag 106.

The genetic material synthesis system 302 may comprise any type of genetic material synthesis system suitable for synthesizing genetic material 304 and/or artificial gene sequences. The genetic material synthesis system 302 may employ a variety of artificial genetic synthesis technologies including, for example, one or more of DNA replication, polymerase chain reaction, oligonucleotide synthesis, annealing-based connection of oligonucleotides, and/or any combination of the same. In certain embodiments, the genetic material synthesis system 302 may be configured to synthesize plasmids that encode information relating to a product 104 in associated genetic sequences.

Operation of the genetic material synthesis system 302 may be controlled, at least in part, by a genetic material product tagging control system 300. The genetic material product tagging control system 300 may be communicatively coupled to the genetic material synthesis system 302 and/or one or more other systems via one or more networks comprising one or more network connections. For example, the genetic material product tagging control system 300 may communicate with a trusted authority 318 maintaining a database 312 storing product and/or associated genetic tag information. The genetic material product tagging control system 300 may further communicate with a genetic material deposition device 306 configured to persistently and/or substantially persistently associate the genetic material 304 with a product 104. Various embodiments disclosed herein are discussed in connection with a genetic material deposition device 306 that comprises a gene gun, although it will be appreciate that other genetic material deposition devices may also be used in connection with the disclosed embodiments.

The genetic material product tagging control system 300, genetic material synthesis system 302, trusted authority 318, genetic material deposition device 306, and/or one or more other associated systems (such as a genetic tag extraction and sequencing system and/or a product information identification system described below) may comprise any suitable computing system or combination of systems configured to implement embodiments of the systems and methods disclosed herein. In certain embodiments, the genetic material product tagging control system 300, genetic material synthesis system 302, trusted authority 318, genetic material deposition device 306, and/or other associated systems may comprise at least one processor system configured to execute instructions stored on an associated non-transitory computer-readable storage medium.

As discussed in more detail below, the genetic material product tagging control system 300, genetic material synthesis system 302, trusted authority 318, genetic material deposition device 306, and/or other associated systems may further comprise a secure processing unit ("SPU") configured to perform sensitive operations such as trusted credential and/or key management, secure policy management and enforcement, and/or other aspects of the systems and methods disclosed herein. The genetic material product tagging control system 300, genetic material synthesis system 302, trusted authority 318, genetic material deposition device 306, and/or other associated systems may additionally comprise software and/or hardware configured to enable electronic communication of information between the systems via one or more associated network connections.

The genetic material product tagging control system 300 may comprise a computing device executing one or more applications and/or software modules 314, 316 configured to implement embodiments of the systems and methods disclosed herein. In certain embodiments, the genetic material product tagging control system 300 may comprise a laptop computer system, a desktop computer system, a smartphone, a tablet computer, and/or any other computing system and/or device that may be utilized in connection with the disclosed systems and methods.

In some embodiments, the genetic material product tagging control system 300 may be communicatively coupled to the genetic material synthesis system 302 and be configured to control the operation thereof. In further embodiments, the genetic material product tagging control system 300 and the genetic material synthesis system 302 may be integrated into a single system. In certain embodiments, the genetic material product tagging control system 300 may comprise software and/or hardware configured to, among other things, control genetic material synthesis operations performed by the genetic material synthesis system 302.

The genetic material product tagging control system 300 may communicate with the trusted authority 318 and/or other systems via one or more networks comprising any suitable number of networks and/or network connections. The network connections may comprise a variety of network communication devices and/or channels and may utilize any suitable communication protocols and/or standards facilitating communication between the connected devices and systems. The network connections may comprise the Internet, a local area network, a virtual private network, and/or any other communication network utilizing one or more electronic communication technologies and/or standards (e.g., Ethernet or the like). In some embodiments, the network connections may comprise a wireless carrier system such as a personal communications system ("PCS"), and/or any other suitable communication system incorporating any suitable communication standards and/or protocols. In further embodiments, the network connections may comprise an analog mobile communications network and/or a digital mobile communications network utilizing, for example, code division multiple access ("CDMA"), Global System for Mobile Communications or Groupe Special Mobile ("GSM"), frequency division multiple access ("FDMA"), and/or time divisional multiple access ("TDMA") standards. In certain embodiments, the network connections may incorporate one or more satellite communication links. In yet further embodiments, the network connections may utilize IEEE's 802.11 standards, Bluetooth®, ultra-wide band ("UWB"), Zigbee®, and or any other suitable communication protocol(s).

Operation of the genetic material synthesis system 302 may be controlled, at least in part, by a control module 316 executing on the genetic material product tagging control system 300. Among other things, the control module 316 may issue one or more control instructions 308 to the genetic material synthesis system 302 in connection with synthesizing genetic information.

In certain embodiments, the instructions for synthesizing genetic material 304 may be based on information provided by a tag sequence generation module 314. The tag sequence generation module 314 may be configured to encode and/or otherwise translate product information into a genetic sequence. As discussed above, the product information may comprise, for example, one or more of information relating to a product 104 (e.g., information identifying a product type, mode, serial number, origin, etc.), information relating to a handling and/or distribution of the product 104 (e.g., provenance information), information relating to real and/or intellectual property rights associated with the product 104, information providing a location and/or link to information associated with the product 104, and/or any other desirable information relating to the product 104. The product information may be encoded and/or otherwise translated into a genetic sequence using a variety of suitable encoding methods for expressing information in a genetic sequence, and it will be appreciated that any suitable method of encoding and/or otherwise expressing information into a genetic sequence may be used in connection with the disclosed embodiments.

Information encoded in a genetic sequence may further comprise one or more error correction codes such as, for example, a cyclic redundancy check. When decoding and/or translating the genetic sequence, described in more detail below, the error correction code may be used to verify the integrity of the encoded information, which may be detrimentally impacted by mutation of the genetic material 304. In certain embodiments, a genetic material 304 such as a plasmid may have a template structure in its associated genetic sequence, and encoded information may be included in certain specified locations in the template. In yet further embodiments, the genetic sequence may be used to encode various digital certificates such as, for example, a public key infrastructure ("PKI") certificate.

The control module 316 may analyze the description of the genetic sequence to be synthesized encoding the product information generated by the tag sequence generation module 314, and may generate control instructions 308 for synthesizing the genetic material based on the capabilities of the genetic material synthesis system 302. That is, the control module 316 may determine how to synthesize the genetic material 304 with the genetic material synthesis system 302 based on a description of the material and/or associated sequence generated by the tag sequence generation module 314.

Based on the received control instructions 308, the genetic material synthesis system 302 may synthesize and/or otherwise generate the associated genetic material 304. The synthesized genetic material may be provided to a genetic material deposition device 306. The genetic material deposition device 306 may be configured to persistently and/or substantially persistently associate the genetic material 304 with a product 104 as a genetic tag 106.

The genetic material 304 may be associated with the product 104 as a genetic tag 106 using a variety of techniques and/or methods and/or genetic material deposition devices 306, which may depend on a type of an associated product 104. For example, the genetic material 304 may be associated with a product 104 by depositing the genetic material 304 on a surface of the product and/or a component thereof via an air stream, an aerosol, a detergent, and/or any other carrier medium. In further embodiments, the genetic material 304 may be incorporated into a material used in the product 104 and/or a component thereof during manufacture of the product 104 and/or its constituent materials and/or components. For example, the genetic material 304 may be mixed into a liquid plastic material, a surface coating, and/or the like.

In further embodiments, the genetic material 304 may be introduced into cells included in and/or deposited on a product 104. For example, the genetic material 304 may be introduced into cells included in a product 104 that comprises a biological and/or agricultural product. When introduced into live cells, the genetic material 304 may persist and/or be reproduced by the cells during division. For example, when a genetic material 304 comprising a plasmid is introduced into a live cell, the plasmid may persist and/or be reproduced by the cell during division. Specifically, when a live cell divides, plasmids included in the cell may be copied such that each daughter cell may receive a copy of each plasmid. If the plasmid is inserted into dead cells, the plasmid may persist in the dead cells but not be replicated.

The genetic material 304 may be introduced into the cells using a variety of suitable genetic material deposition devices 306 including, without limitation, a biolistic particle delivery system such as a gene gun. In some embodiments, genetic material 304 may be attached to carrier pellets and/or particles and introduced into the cells using the biolistic particle delivery system. For example, a gene gun may be used to introduce genetic material 304 comprising plasmids attached to microscopic gold and/or other metal carrier particles into cells associated with a product 104. In further embodiments, the genetic material 304 may be introduced into a product 104 and/or using an electrostatic process.

In some embodiments, the genetic material 304 may be associated with information (e.g., product information) that is not necessarily directly encoded in the genetic sequence included in the genetic material 304. For example, when genetic material 304 is associated with a product 104 as a genetic tag 106, information associated with the product 104 and/or the genetic tag 106 may be generated by the genetic material product tagging control system 300 and/or the genetic material deposition device 306. The information may be generated by the system 300 and/or device 306 automatically. In further embodiments, the information may be entered by a user of an associated system 300 and/or device 306.

In an illustrative example, a genetic tag 106 may comprise genetic material 304 that encodes a unique number and/or string. The unique number and/or string may function like a serial number and/or model number associated with the product 104. When the product 104 is associated with the genetic tag 106, information relating to the product 104 that is not necessarily encoded in the genetic tag 106 may be electronically associated with the information that is encoded in the genetic tag 106. The information encoded in the genetic material 304 of the genetic tag 106—generally referred to herein as "tag information"—and/or any related additional product information 310 may be stored by the genetic material product tagging control system 300.

In certain embodiments, the tag information and/or associated product information 310 may be generated by the genetic material deposition device 306 and communicated to the genetic material product tagging control system 300. For example, as part of a product tagging process, a user of the genetic material deposition device 306 may enter information relating to a particular genetic material 304 being used to tag the product 104 and/or various information describing product 104. The tag information may be electronically associated and communicated to the genetic material product tagging control system 300 for storage and/or management.

In certain embodiments, tag and associated product information 310 may be communicated to the trusted authority 318. Tag and product information 310 provided to the trusted authority 118 may be stored, managed, and/or maintained by the trusted authority 318 in a database 312 storing product and/or associated genetic tag information. In some embodiments, the product and genetic tag database 312 may store tag and product information associated with a plurality of genetic tags 106 and/or products 104 and/or information received from a plurality of genetic material product tagging control systems 300 and/or associated genetic material deposition devices 306. In this manner, the trusted authority 318 may operate as a centralized repository storing information relating to a variety of products 104, genetic tags 106, and/or associated genetic material 304 from a variety of associated systems.

As discussed in more detail below, certain contents of the product and genetic tag database 312 may be communicated to one or more requesting systems following extraction of genetic material 304 from a genetic tag 106 for use in connection with various product information distribution systems and methods. For example, contents of the product and genetic tag database 312, including product information associated with a genetic tag 106 extracted from a product 104, may be communicated from the trusted authority 318 in response to received requests issued as part of a product information distribution process, a product provenance checking process, a quality assurance process, and/or the like.

In some embodiments, the various systems and/or 300, 302, 306, 318 and/or associated modules, stored information, and/or databases 310-316 may be associated with a trusted boundary. Including devices, modules, information, databases, and/or systems in a trusted boundary may ensure integrity of the devices, modules, information, databases, and/or systems and/or information communicated therebetween, thereby providing a measure of trust by reducing the potential for nefarious tampering with the various devices, modules, information, databases, and/or systems. For example, in some embodiments, product information may be cryptographically associated with tag information in connection with the storage and transmission of such data in a manner that, for example, would make it difficult to tamper with product information associated with a particular genetic tag 106. In this manner, information included in a genetic tag 106 and/or accessed using information included in a genetic tag 102 may be trusted.

It will be appreciated that a number of variations can be made to the architecture and relationships presented in connection with FIG. 3 within the scope of the inventive body of work. For example, without limitation, in some embodiments, some or all of the functions performed the various systems and/or devices 300, 302, 306, 318 may be performed by a single system and/or device and/or any combination of systems and/or devices. Thus it will be appreciated that the architecture and relationships illustrated in FIG. 3 are provided for purposes of illustration and explanation, and not limitation.

Extraction of Product Information from Tagged Products

Figure 4:
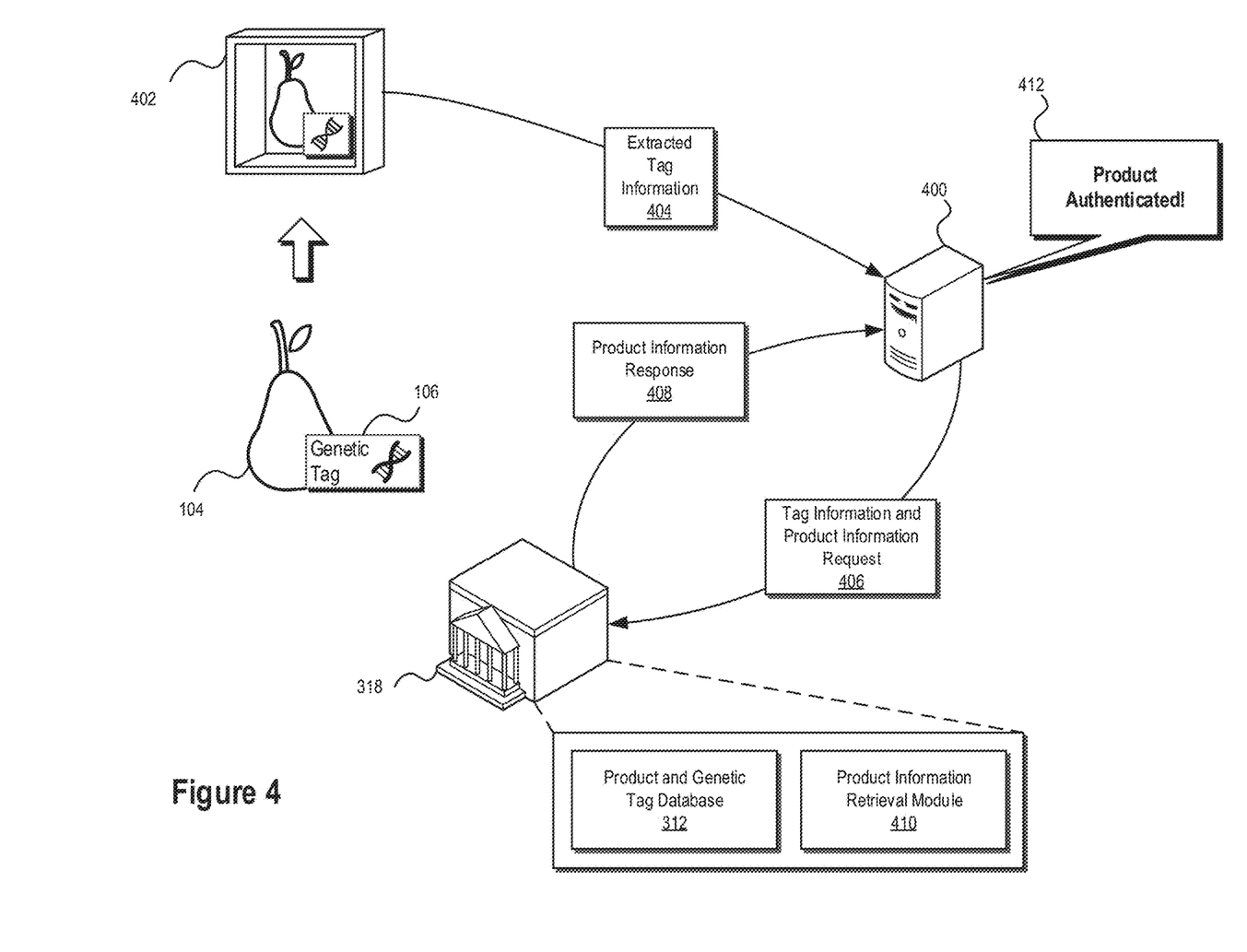
FIG. 4 illustrates extraction of information from a product tagged with genetic material consistent with embodiments of the present disclosure.

FIG. 4 illustrates extraction of information from a product 104 tagged with genetic material consistent with embodiments of the present disclosure. In various embodiments disclosed herein, genetic material included in a genetic tag 106 associated with a product 104 may be extracted from the product 104 and sequenced by a genetic tag extraction and sequencing system 402. Although illustrated as a single system 402 that performs both extraction of genetic material included in a genetic tag 106 and sequencing of the genetic material, it will be appreciated that extraction and sequencing operations may be performed by and/or coordinated between any suitable number of systems.

The genetic tag extraction and sequencing system 402 may first extract genetic material included in the genetic tag 106 from the product 104. For example, the genetic tag extraction and sequencing system 402 may identify a physical location of the genetic tag 106 on the product 104. Once identifying the physical location of the genetic tag, the genetic tag extraction and sequencing system 402 may remove at least a portion of the genetic material associated with the genetic tag 106.

In certain embodiments, the genetic tag extraction and sequencing system 402 may identify the physical location of the genetic tag 106 on the product 104 based on an identified location of one or more detectable markers on the product 104 associated with the genetic tag 106 (e.g., visible markers, markers that are visible under ultraviolet light, color markers, textural markers, etc.). In further embodiments, the genetic tag extraction and sequencing system 402 may identify the physical location of the genetic tag 106 on the product 104 by based on prior knowledge and/or information of the product 104. For example, a particular product 104, if authentic, may be marked by an authentic genetic tag 106 in a particular tag location on the product 104 (e.g., a particular surface, feature, component, and/or the like). Accordingly, using such information, the genetic tag extraction and sequencing system 402 may identify the tag location on the product 104 and extract at least a portion of the genetic material included in the genetic tag 106.

After extracting the genetic material from the genetic tag 106, the genetic tag extraction and sequencing system 402 may sequence the genetic material. The genetic tag extraction and sequencing system 402 may comprise any type of genetic sequencing system suitable for identifying and/or otherwise generating a genetic sequence associated with a genetic material—that is, any suitable system for determining the order of nucleotides within a DNA molecular of a genetic material. The genetic tag extraction and sequencing system 402 may employ a variety of gene sequencing technologies including, for example, one or more of Maxam-Gilbert sequencing, chain-termination sequencing, shotgun sequencing, bridge PCR sequencing, single-molecular real-time sequencing, ion semiconductor sequencing, pyrosequencing, sequencing by synthesis, sequencing by ligation, nanopore sequencing, chain termination sequencing, massively parallel signature sequencing, polony sequencing, parallelized pyrosequencing, dye sequencing, DNA nanoball sequencing, heliscope single molecule sequencing, single-molecule real-time sequencing, and/or any other type of genetic sequencing technology and/or process.

The genetic tag extraction and sequencing system 402 may be communicatively coupled with a product information identification system 400. In certain embodiments, certain operations of the genetic tag extraction and sequencing system 402 may be coordinated, at least in part, by the product information identification system 400. The product information identification system 400 may be further communicatively coupled with the trusted authority 318, and may interact in connection with identifying information associated with the product 104 consistent with the disclosed embodiments.

Extracted tag information 404 from the genetic tag 106 associated with the product 104 that is generated by the genetic tag extract and sequencing system 402 may communicated to the product information identification system 400. In certain embodiments, the extracted tag information 404 may comprise a genetic sequence associated with the extracted genetic material included in the genetic tag 106. In further embodiments, the extracted tag information 404 may comprise information that is translated from a genetic sequence associated with the extracted genetic material included in the genetic tag 106. For example, in some embodiments, a genetic sequence associated with the extracted genetic material included in the genetic tag 106 may be translated and/or otherwise transformed using an applicable encoding/decoding and/or translation methodology (e.g., a translation code providing a system of rules to convert the genetic sequence information into product information), and the translated and/or transformed information may be provided to the product information identification system 400 as extracted tag information 404.

Using the received extracted tag information 404, the product information identification system 400 may generate and issue a request 406 to the trusted authority 318. In certain embodiments, the request 406 may comprise the received extracted tag information 404 and/or information derived therefrom. A product information retrieval module 410 executed by the trusted authority may receive the request 406, and generate and return a product information response 408 to the product information identification system 400 based on the request 406.

For example, in some embodiments, the product information retrieval module 410 may identify information included in a product information and genetic tag database 312 managed by the trusted authority 318 associated with the tag information received in the request 406, and may return the information to the product information identification system 400 as part of the product information response 408. In this manner, the trusted authority 318 may identify product information included in the database 312 based on the information extracted and sequenced from the genetic tag 106, and return the product information to an interested user. In certain embodiments, a user may be provided with an indication 412 of the returned product information. For example, in connection with a product authentication process, a user may be provided with an indication 412 regarding whether a product associated with a tag and product information request 406 is an authentic product.

It will be appreciated that a number of variations can be made to the architecture and relationships presented in connection with FIG. 4 within the scope of the inventive body of work. For example, without limitation, in some embodiments, some or all of the functions performed the various systems 318, 400, 402 may be performed by a single system and/or device and/or any combination of systems and/or devices. Thus it will be appreciated that the architecture and relationships illustrated in FIG. 4 are provided for purposes of illustration and explanation, and not limitation.

Example—Product Validation

Embodiments of the disclosed systems and methods may be used in connection with a variety of contexts and/or processes including, without limitation, provenance tracking and product registration, chain of custody identification, product transactions, and product information distribution (e.g., serial number) processes. For example, in connection with a purchase transaction, a user may wish to, among other things, validate that a product is an authentic product from its manufacturer and not a counterfeit, confirm that the product is new or was not sold previously as new, obtain ownership history information regarding the product, and/or the like. Consistent with embodiments disclosed herein, the user may obtain such information by extracting and analyzing genetic information included in and/or otherwise associated with the product.

Example—Quality Assurance

Embodiments of the disclosed systems and methods may be further used in connection with food and/or agricultural quality assurance methods. In one example, an agricultural producer may create a unique agricultural product (e.g., a parsnip and/or parsnip seeds) following substantial research efforts. To establish a unique brand, enforce any intellectual property rights to their creation, and/or realize a return on their investment, the producer may contact a certification authority. The certification authority may inspect the quality of the product and, if it meets its quality standards, tag the with a plasmid marker indicating its certification of the product and/or a unique identifier associated with the product (e.g., a serial number and/or the like). In certain embodiments, the certification authority may tag the product with the plasmid marker using, for example, a gene gun configured to insert generated plasmids attached to carrier pellets (e.g., microscopic gold pellets) into live cells of the agricultural product. When planted and allowed the reproduce, the inserted plasmids may persist across multiple generations of the agricultural product, thereby providing an indication of the provenance of the product.

Example—Chain of Handling Assurance

Embodiments of the disclosed systems and methods may be further used in connection with chain of handling assurance methods. In an example, a food handling company may be concerned that relatively inexpensive imported products on the market may be undermining their ability to distinguish food products they handle based on quality, and may wish to assure that any food products passing through their facility are indelibly marked as such. A certification authority may inspect the food handling facility and, if it meets certain stands standards, provide the food handling company with a plasmid marker tag and/or an insertion mechanism for introducing into food products that pass through its facility. The plasmid marker tag may be used to verify that a food product was handled by the facility consistent with embodiments of the disclosed systems and methods.

Figure 5:
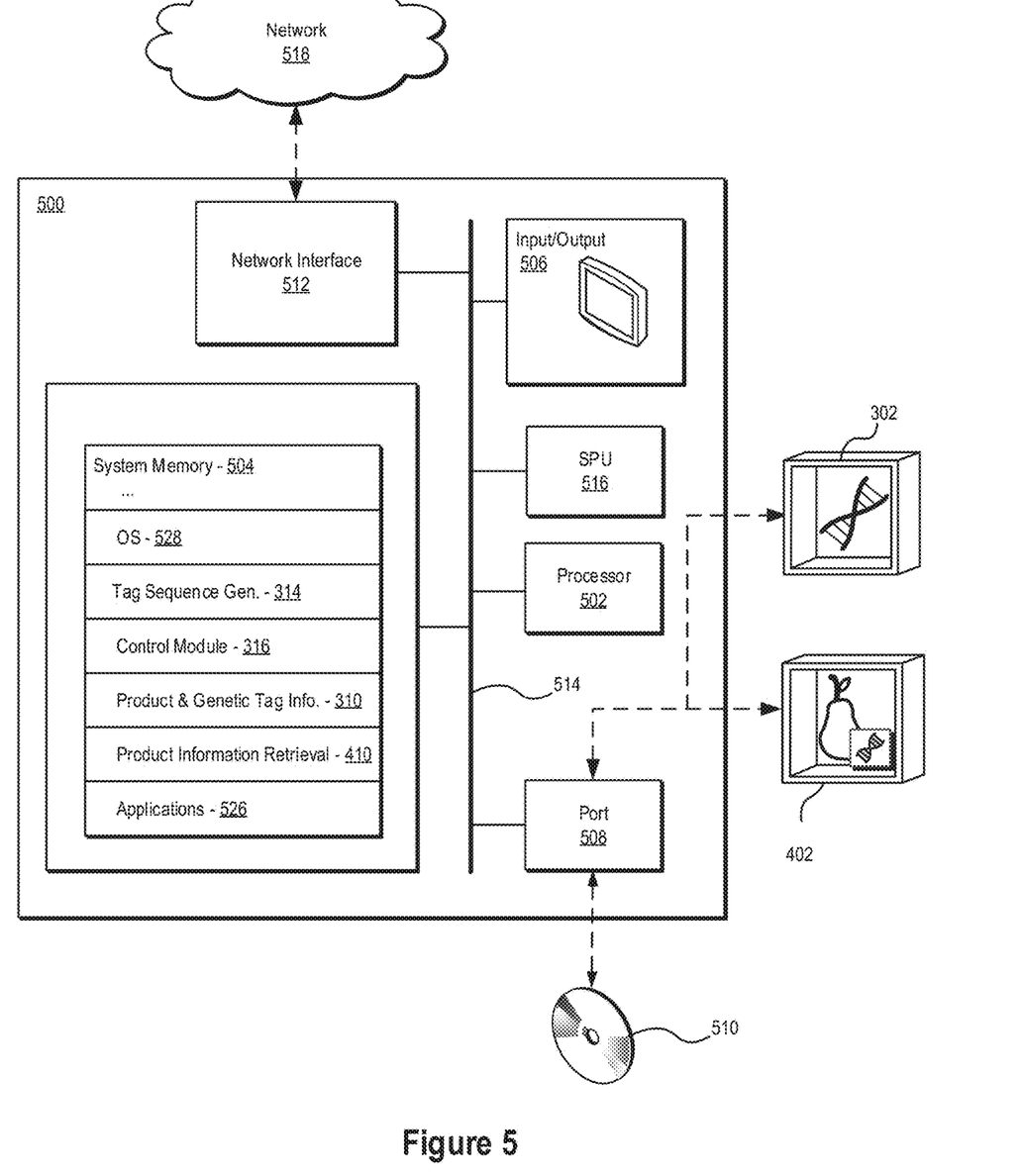
FIG. 5 illustrates a system that may be used to implement certain embodiments of the systems and methods of the present disclosure.

FIG. 5 illustrates a system 500 that may be used to implement certain embodiments of the systems and methods of the present disclosure. The system 500 may comprise a laptop computer system, a desktop computer system, a server computer system, and/or any other system or device configured to implement the systems and methods described herein. In certain embodiments, the system 500 may perform certain functions associated with a genetic material product tagging control system, a genetic material synthesis system 302, a genetic material deposition device, a trusted authority, a genetic tag extraction and sequencing system 402, a product information identification system, and/or any other system and/or device described herein.

As illustrated in FIG. 5, the system 500 may include: a processor 502; system memory 504, which may include high speed RAM, non-volatile memory and/or one or more bulk non-volatile computer-readable storage mediums (e.g., a hard disk, flash memory, etc.) for storing programs and other data for use and execution by the processor 502; an interface 506 (e.g., an input/output interface) that may include a display and/or one or more input devices such as, for example, a touchscreen, a keyboard, a mouse, a track pad, and the like; a port for interfacing 508 with removable memory 510 that may include one more diskettes, optical storage mediums, and/or other computer-readable storage mediums (e.g., flash memory, thumb drives, USB dongles, compact discs, DVDs, etc.), a genetic material synthesis system 302, and/or a genetic tag extraction and sequencing system 402; a network interface 512 for communicating with other systems via a network 518 using one or more communication technologies; and one or more buses 514 for communicatively coupling the aforementioned elements.

In some embodiments, the system 500 may, alternatively or in addition, include a SPU 516 that is protected from tampering by a user of the system 500 or other entities by utilizing secure physical and/or virtual security techniques. An SPU 516 can help enhance and/or facilitate the security of sensitive operations such as private management and/or enforcement of policies and/or other aspects of the systems and methods disclosed herein. In certain embodiments, the SPU 516 may operate in a logically secure processing domain and be configured to protect and/or operate on secret information. In some embodiments, the SPU 516 may include internal memory storing executable instructions or programs configured to enable to the SPU 516 to perform secure operations.

The operation of the system 500 may be generally controlled by the processor 502 by executing software instructions and programs stored in the system memory 504 (and/or other computer-readable media, such as removable memory). The system memory 504 may store a variety of executable programs or modules for controlling the operation of the system. For example, the system memory 504 may include an operating system ("OS") 528 that may manage and coordinate, at least in part, system hardware resources and provide for common services for execution of various functions. The system memory 504 may further include, without limitation, a tag sequence generation module 314 configured to encode and/or otherwise translate product information into a genetic sequence, a control module 316 configured to issue one or more control instructions to a genetic material synthesis system 302 and/or the genetic tag extraction and sequencing system 402, product and/or genetic tag information 310, a product information retrieval module 410 configured to process product information requests and return associated responses, and/or any other information, modules, and/or applications 526 configured to implement embodiments of the systems and methods disclosed herein.

One of ordinary skill in the art will appreciate that the systems and methods described herein can be practiced with computing devices similar or identical to that illustrated in FIG. 5, or with virtually any other suitable computing device, including computing devices that do not possess some of the components shown in FIG. 5 and/or computing devices that possess other components that are not shown. Thus, it should be appreciated that FIG. 5 is provided for purposes of illustration and not limitation.

The systems and methods disclosed herein are not inherently related to any particular computer, electronic control unit, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions, that when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a magnetic disk, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims

What is claimed is:

1. A method for securely associating information with a product, the method comprising:
generating initial product information associated with the product;
electronically associating the initial product information with tag information, the tag information being encoded in genetic material included in a genetic tag, the genetic material comprising at least one of a plasmid and a bacterium;
transmitting the electronically associated initial product information and tag information to a remote trusted authority system for storage; and
depositing the genetic tag on the product using a genetic material deposition device.

2. The method of claim 1, wherein the method further comprises retrieving the tag information.

3. The method of claim 1, wherein the tag information is encoded in a genetic sequence of the genetic material included in the genetic tag.

4. The method of claim 1, wherein the tag information comprises a unique string value associated with the genetic tag.

5. The method of claim 1, wherein the tag information comprises location information associated with the remote trusted authority system.

6. The method of claim 1, wherein the tag information comprises information that is used to retrieve the initial product information from the remote trusted authority system.

7. The method of claim 1, wherein electronically associating the initial product information with the tag information comprises securely associating the initial product information with the tag information.

8. The method of claim 7, wherein securely associating the initial product information with the tag information comprises cryptographically associating the initial product information with the tag information and wherein transmitting the electronically associated initial product information and tag information comprises transmitting the cryptographically associated initial product information and tag information to the remote trusted authority system for storage.

9. The method of claim 1, wherein depositing the genetic tag on the product comprises depositing the genetic tag proximate to a location marker on the product.

10. The method of claim 9, wherein the location marker comprises at least one of a visible location marker, an ultraviolet location marker, and a textural location marker.

11. The method of claim 1, wherein depositing the genetic tag on the product comprises introducing the genetic material into at least one cell of the product.

12. The method of claim 1, wherein the product comprises at least one of an agricultural product and a live cell line product.

13. The method of claim 1, wherein the genetic material deposition device comprises a biolistic particle delivery device.

14. The method of claim 1, wherein the genetic material deposition device comprises an electrostatic genetic material deposition device.

15. The method of claim 1, wherein the initial product information comprises product provenance information.

16. The method of claim 1, wherein the initial product information comprises product ownership information.

17. The method of claim 1, wherein the initial product information comprises product description information.

18. The method of claim 1, wherein the method further comprises synthesizing the genetic material to generate the genetic tag.

19. The method of claim 18, wherein synthesizing the genetic material comprises encoding the tag information in at least one genetic sequence of the genetic material.

20. The method of claim 19, wherein encoding the tag information in the at least one genetic sequence comprises encoding the tag information in the at least one genetic sequence using, at least in part, a translation code.

\* \* \* \* \*